(12) United States Patent
Mogi et al.

(10) Patent No.: US 8,747,965 B2
(45) Date of Patent: Jun. 10, 2014

(54) PRECURSOR FOR FORMATION OF EUROPIUM-CONTAINING THIN FILM, AND METHOD FOR FORMING EUROPIUM-CONTAINING THIN FILM

(75) Inventors: Takayuki Mogi, Sakado (JP); Yoshinori Kuboshima, Sakado (JP); Shintaro Higashi, Sakado (JP); Kaoru Kikukawa, Sakado (JP)

(73) Assignee: Kabushikikaisha Kojundokagaku Kenkyusho, Sakado-shi (JP)

( * ) Notice: Subject to any disclaimer, the term of this patent is extended or adjusted under 35 U.S.C. 154(b) by 0 days.

(21) Appl. No.: 14/007,474

(22) PCT Filed: Feb. 23, 2012

(86) PCT No.: PCT/JP2012/054388
§ 371 (c)(1),
(2), (4) Date: Sep. 25, 2013

(87) PCT Pub. No.: WO2012/132669
PCT Pub. Date: Oct. 4, 2012

(65) Prior Publication Data
US 2014/0024814 A1 Jan. 23, 2014

(30) Foreign Application Priority Data
Mar. 29, 2011 (JP) ................. 2011-071397

(51) Int. Cl.
B05D 3/06 (2006.01)
C23C 18/00 (2006.01)
C23C 18/14 (2006.01)
C23C 20/00 (2006.01)

(52) U.S. Cl.
USPC ........................................ 427/581

(58) Field of Classification Search
None
See application file for complete search history.

(56) References Cited

U.S. PATENT DOCUMENTS

| 7,759,746 B2 | 7/2010 | Clark |
| 2007/0235821 A1 | 10/2007 | Clark |
| 2007/0235822 A1 | 10/2007 | Clark |
| 2009/0001618 A1 | 1/2009 | Kadokura et al. |

FOREIGN PATENT DOCUMENTS

JP 2009-030162 A 2/2009

OTHER PUBLICATIONS

Evans, Metal Vapor Synthesis of (C5Me5)2Sm(THF)2 and (C5Me4Et)2Sm(THF)2 and Their Reactivity and Organomercurial Reagents. Synthesis and X-ray Structural Analysis of (C5Me5)2Sm(C6H5)(THF), Organometallics, 1985, 4, 112-119.*
West, Gary, A, et al., "Low-pressure metalorganic chemical vapor deposition of photoluminescent Eu-doped Y2O3 films", J. Mater. Res., 1990, vol. 5, No. 7, pp. 1573-1580, cited in Specification.

(Continued)

Primary Examiner — Paul Dickinson
(74) Attorney, Agent, or Firm — Westerman, Hattori, Daniels & Adrian, LLP

(57) ABSTRACT

Provided are a novel europium compound which has a melting point of 180° C. or lower and can be stably supplied by bubbling in a chemical vapor deposition method or an atomic layer deposition method, a precursor for forming a europium-containing thin film based on the compound, and a method for forming a europium-containing thin film using this precursor. A europium-containing thin film is formed using bis(tetramethylmonoalkylcyclopentadienyl)europium as a precursor for forming a europium-containing thin film by a chemical vapor deposition method or anatomic layer deposition method.

8 Claims, 6 Drawing Sheets

(56) References Cited

OTHER PUBLICATIONS

Paivasaari, Jani, et al., "A comparative study on lanthanide oxide thin films grown by atomic layer deposition", Thin Solid Films 472, 2005, pp. 275-281, cited in Specification.

International Search Report dated May 22, 2012, issued in corresponding application No. PCT/JP2012/054388.

* cited by examiner

PRECURSOR FOR FORMATION OF EUROPIUM-CONTAINING THIN FILM, AND METHOD FOR FORMING EUROPIUM-CONTAINING THIN FILM

TECHNICAL FIELD

The present invention relates to a precursor suitable for the formation of a europium-containing thin film as a gate insulating film or an optical material thin film, and a method for forming a europium-containing thin film using this precursor.

BACKGROUND ART

Regarding thin films containing europium, thin films obtained by adding europium to a gate insulating film or adding europium to an optical material, are known (see, for example, Patent Literature 1 and Non-Patent Literature 1).

Regarding the precursor that is used when these europium-containing thin films are formed by a chemical vapor deposition method (hereinafter, abbreviated to CVD method) or an atomic layer deposition method (hereinafter, abbreviated to ALD method), trisdipivaloylmethanatoeuropium (hereinafter, abbreviated to $Eu(dpm)_3$) and europium fluorinated β-diketonate (hereinafter, abbreviated to $Eu(hfac)_3$) are known (see Non-Patent Literature 2).

Furthermore, Patent Literature 1 describes film formation using tricyclopentadienyleuropium (hereinafter, abbreviated to $Eu(Cp)_3$), which is a trivalent cyclopentadienyl-based compound, or $Eu[C_5(CH_3)_5]_2$, which is a divalent cyclopentadienyl-based compound.

CITATION LIST

Patent Literature

Patent Literature 1: U.S. Pat. No. 7,759,746

Non-Patent Literature

Non-Patent Literature 1: Gary A. West, K. W. Beeson, J. Mater. Res. (1990), Vol. 5, Issue 7, pp. 1573-1580

Non-Patent Literature 2: J. Paivasaari, M. Putkonen, L. Niinisto, Thin Solid Films 472, 275 (2005)

SUMMARY OF INVENTION

Technical Problem

Generally, a raw material container and piping used in a CVD method or an ALD method are set to be at 180° C. or lower, due to the problem of the heat resistance of valves and the like.

However, $Eu(dpm)_3$ has a melting point as high as 187° C. to 189° C. at a vapor pressure of 0.1 torr/180° C. Therefore, when this precursor is supplied to a film forming apparatus, it has been necessary to supply the precursor after sublimating the precursor. The amount of supply by the sublimation method varies depending on the shape of a solid in the raw material container, and since the shape varies with the supply, stable supply has been difficult.

Furthermore, in order to prevent blocking of the piping due to solidification of the raw material, the piping extending from the raw material container to the chamber must be maintained at a temperature higher by about 20° C. than the temperature of the raw material container.

Also, in the film formation according to an ALD method, since thermal decomposition occurs at about 300° C. which is equivalent to the substrate temperature, there has been a problem that film formation may occur by mechanisms other than atomic layer deposition, and films containing impurities are prone to be formed. Furthermore, since reactivity with water is low, water is not suitable as an oxidizing agent. Therefore, it is necessary to use $O_3$ as the oxidizing agent, but there has also been a problem that carbon compounds produced as a result of the decomposition of the dpm group may be easily incorporated into the film.

On the other hand, $Eu(hfac)_3$ has a higher vapor pressure and can be supplied as a raw material more easily as compared with $Eu(dpm)_3$; however, in terms of other matters, this compound has the same problem as $Eu(dpm)_3$.

Furthermore, since β-diketonate-based compounds such as $Eu(dpm)_3$ and $Eu(hfac)_3$ contain oxygen in the molecules, the compounds can be basically used only for the formation of oxide films.

Furthermore, since trivalent cyclopentadienyl-based europium compounds are thermally unstable and are decomposed in a raw material container or in a vaporizer, those compounds cannot be used in a CVD method or an ALD method.

Also, $Eu[C_5(CH_3)_5]_2$ which is a divalent cyclopentadienyl-based europium compound has a melting point as high as 211° C., and therefore, it needs to be supplied by the sublimation method. Thus, this also has a problem in terms of stability in supply, similarly to Eu $(dpm)_3$.

Furthermore, since europium precursors of the related art such as described above do not liquefy but sublime due to the relationship between the melting point and the vapor pressure, it has been difficult to carry out purification by distillation, and it has been difficult to obtain precursor compounds with high purity.

Therefore, it has been requested that europium precursors for film formation have high thermal stability, have a melting point of 180° C. or lower, and be capable of stable supply by bubbling. Furthermore, it is desired that water can be used as an oxidizing agent, and the precursors can be purified by distillation, do not contain oxygen, and can form films of nitrides or sulfides.

The inventors of the invention conducted investigations on europium precursors that are adequate for the formation of europium-containing thin films according to a CVD method or an ALD method, based on these matters. As a result, the inventors contemplated that divalent cyclopentadienyl-based europium compounds are stable to heat and react rapidly with water, and therefore, these compounds are promising as europium precursors for a CVD method or an ALD method. Thus, the inventors found a novel europium compound which was obtained by improving $Eu[C_5(CH_3)_5]_2$ that is known in the related art.

That is, an object of the invention is to provide a novel europium compound which has a melting point of 180° C. or lower and can be stably supplied by bubbling in a CVD method or an ALD method, a precursor for forming a europium-containing thin film based on the europium compound, and a method for forming a europium-containing thin film using this precursor.

Solution to Problem

According to the invention, there is provided bis(tetramethylmonoalkylcyclopentadienyl) europium which is a novel europium compound and is represented by $Eu[C_5(CH_3)_4R]_2$ (wherein R represents an alkyl group having 2 or more carbon atoms).

Since there has been hitherto no report on the synthesis or properties of $Eu[C_5(CH_3)_4R]_2$, this europium compound is a novel chemical substance.

R in the formula: $Eu[C_5(CH_3)_4R]_2$ is preferably an alkyl group having 2 to 5 carbon atoms.

More preferably, R is any of an ethyl group, an n-propyl group, an n-butyl group and an n-pentyl group. That is, $Eu[C_5(CH_3)_4R]_2$ is more preferably any of $Eu[C_5(CH_3)_4(C_2H_5)]_2$, $Eu[C_5(CH_3)_4(n-C_3H_7)]_2$, $Eu[C_5(CH_3)_4(n-C_4H_9)]_2$ and $Eu[C_5(CH_3)_4(n-C_5H_{11})]_2$.

Furthermore, according to the invention, a precursor for forming a europium-containing thin film according to a CVD method or an ALD method based on the above-mentioned $Eu[C_5(CH_3)_4R]_2$ is provided.

$Eu[C_5(CH_3)_4R]_2$ can serve as a precursor which has a melting point of 180° C. or lower, is capable of being supplied as a material by bubbling, and is suitable for the formation of a europium-containing thin film according to a CVD method or an ALD method.

Furthermore, according to the invention, there is provided a method for forming a europium-containing thin film using the precursor for forming a europium-containing thin film.

As described above, $Eu[C_5(CH_3)_4R]_2$ can be suitably used for the formation of a europium-containing thin film according to a CVD method or an ALD method.

Advantageous Effects of Invention $Eu[C_5(CH_3)_4R]_2$ according to the invention is a novel europium compound, and has excellent stability to heat as compared with the europium compounds that have been used as europium-containing thin film precursors of the related art. Also, the compound has a melting point of 180° C. or lower, and can be stably supplied by bubbling. Furthermore, since the compound is highly reactive with an oxidizing agent, and water can be used as the oxidizing agent, the film hardly contains carbon. Furthermore, since the compound can be purified by distillation, the compound also has an advantage that purification is carried out easily, and mass productivity is excellent.

Therefore, $Eu[C_5(CH_3)_4R]_2$ is a europium compound which is suitable as a precursor for forming a europium-containing thin film according to a CVD method or an ALD method. Furthermore, since $Eu[C_5(CH_3)_4R]_2$ does not contain oxygen in the molecule, a europium-containing thin film of a nitride, a sulfide or the like, which does not contain oxygen, can be suitably formed.

DESCRIPTION OF EMBODIMENT

Figure 1:
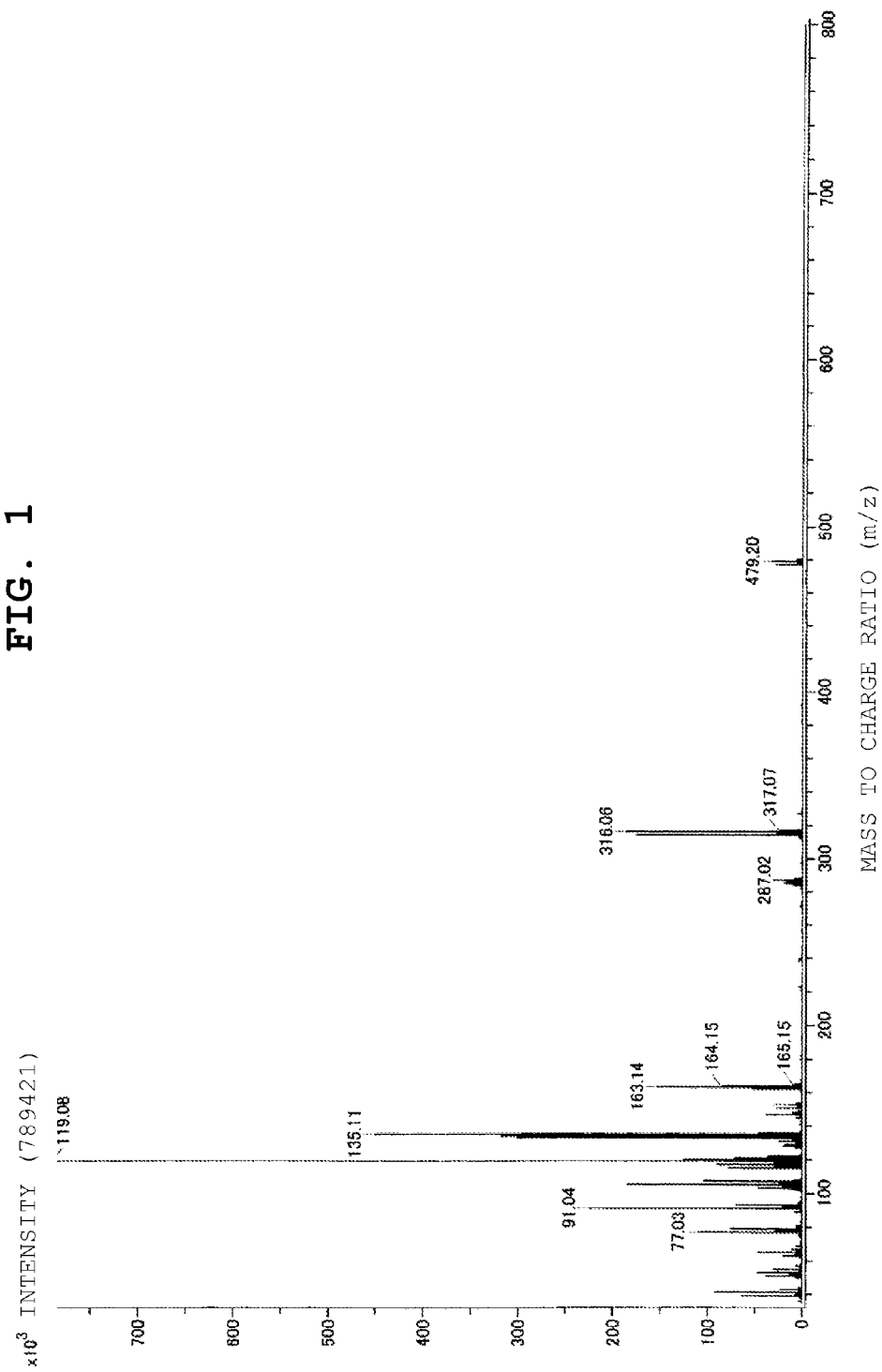
FIG. 1 is a spectrum of electron ionization-mass spectrometry (EI-MS) of a sample $(Eu[C_5(CH_3)_4(n-C_3H_7)]_2)$ obtained in Example 1.

Hereinafter, the invention will be described in detail.

$Eu[C_5(CH_3)_4R]_2$ according to the invention is a novel europium compound for which no report has been made hitherto on the synthesis or properties of the compound. Therefore, it is not known that this compound has a melting point of 180° C. or lower, can be supplied by bubbling in a CVD method or an ALD method, and can serve as a precursor for forming a europium-containing thin film.

$Eu[C_5(CH_3)_4R]_2$ can be produced by the following two synthesis methods.

A first production method is a method of allowing Eu metal to react with tetramethylmonoalkylcyclopentadiene (hereinafter, indicated as $C_5(CH_3)_4RH$) in liquid ammonia.

At this time, regarding the reaction solvent, ethers such as diethyl ether, tetrahydrofuran (hereinafter, abbreviated to THF) and dibutyl ether; saturated aliphatic hydrocarbons such as pentane, hexane and octane; and aromatic hydrocarbons such as benzene, toluene and xylene can be used singly or as mixtures. Preferably, a solvent containing toluene having high solubility in liquid ammonia is used.

The reaction temperature is set to a temperature at which ammonia can exist as liquid, and preferably, when the reaction is carried out at normal pressure, the reaction temperature is set to a temperature slightly lower than the boiling point of ammonia.

After the reaction, an ether is added to dissolve the product as an ether adduct, and then any unreacted substances are separated by filtration. Then, the filtrate is distilled off under reduced pressure at 60° C. to 200° C., and the solvent and the ether that has been attached are removed. Thereby, a crude product of $Eu[C_5(CH_3)_4R]_2$ is obtained.

A second production method is a method of allowing an alkali metal hydride to react with $C_5(CH_3)_4RH$ to synthesize $MC_5(CH_3)_4R$ (provided that M represents an alkali metal element), and allowing this to react with anhydrous $EuI_2$.

Examples of the alkali metal hydride that can be used include NaH or KH. LiH is not preferable because it does not cause the reaction to fully proceed.

Anhydrous $EuI_2$ is preferably a substance having a water content of 100 ppm or less.

Examples of the reaction solvent that can be used in this case include solvents containing ethers such as diethyl ether, THF, and dibutyl ether.

After the reaction, the solvent is replaced with an extraction solvent, and any unreacted substances are separated by filtration. As the extraction solvent, a mixed solvent of ethers and a saturated aliphatic hydrocarbon or an aromatic hydrocarbon is used. Preferably, a mixed solvent of THF and toluene is used. Then, the filtrate is distilled off under reduced pressure at 60° C. to 200° C., and the solvent and the ether that has been attached are removed. Thereby, a crude product of $Eu[C_5(CH_3)_4R]_2$ is obtained.

Meanwhile, in both of the two synthesis methods, it should be noted that if the filtrate is not completely distilled off, the ether is not completely detached from the ether adduct.

When crude $Eu[C_5(CH_3)_4R]_2$ obtained by the synthesis methods described above is distilled at 160° C. to 230° C. and 0.001 torr to 1 torr, high purity $Eu[C_5(CH_3)_4R]_2$ is obtained as a distillate.

The melting point of $Eu[C_5(CH_3)_4(C_2H_5)]_2$ is 122.4° C., the melting point of $Eu[C_5(CH_3)_4(n-C_3H_7)]_2$ is 49.1° C., and the melting point of $Eu[C_5(CH_3)_4(n-C_4H_9)]_2$ is 31.7° C. $Eu[C_5(CH_3)_4(n-C_5H_{11})]_2$ is a liquid that is highly viscous at room temperature. In order to prevent blocking of the distillation apparatus, the site where the distillate is cooled and collected is preferably at about 55° C. to 130° C. Furthermore, since about 3% of the first distillate fraction contains the solvent or the attached ether, it is preferable to eliminate the portion. Furthermore, in order to completely eliminate the ether that has been attached in a small amount, it is preferable to repeat distillation two or more times.

When $Eu[C_5(CH_3)_4R]_2$ obtained by the methods described above is used as a raw material (precursor) for film formation, oxides, nitrides and sulfides containing europium can be suitably formed by a CVD method or an ALD method.

Regarding the method for supplying $Eu[C_5(CH_3)_4R]_2$ at the time of film formation, a method of heating $Eu[C_5(CH_3)_4R]_2$ to 100° C. to 180° C. to obtain a flowable liquid, and vaporizing the compound by bubbling a carrier gas; or a method of dissolving $Eu[C_5(CH_3)_4R]_2$ in an inert hydrocarbon solvent, supplying the solution with a liquid mass flow meter, and vaporizing the entire amount in a vaporizer at 170° C. to 350° C., can be used.

The solvent that is used at this time is preferably an aromatic hydrocarbon having relatively high solubility, and particularly, a solvent with a high boiling point such as tetralin is preferred.

When the vapor of $Eu[C_5(CH_3)_4R]_2$ that has been vaporized by a method as described above, and oxygen, $O_3$, water or the like as an oxidizing agent are used, a $Eu_2O_3$ film can be formed by a CVD method or an ALD method.

Furthermore, when the vapor of $Eu[C_5(CH_3)_4R]_2$, and a nitride such as ammonia or hydrazine as a nitrifying agent are used, a europium nitride film can be formed by a CVD method or an ALD method.

Also, when the vapor of $Eu[C_5(CH_3)_4R]_2$, and a sulfide such as hydrogen sulfide as a sulfurizing agent are used, a europium sulfide film can be formed by a CVD method or an ALD method.

EXAMPLES

Hereinafter, the invention will be described more specifically by way of Examples, but the invention is not intended to be limited to the following Examples.

Example 1

Synthesis of $Eu[C_5(CH_3)_4(n-C_3H_7)]_2$ (Liquid Ammonia Method)

In a 1-L four-necked flask, 400 ml of dehydrated toluene, 20.7 g (0.136 mol) of Eu metal, and 53.6 g (0.33 mol) of $C_5(CH_3)_4(n-C_3H_7)H$ were introduced, and the mixture was cooled to a temperature of −70° C. or lower. While about 150 g of ammonia gas was slowly blown into this mixture, the mixture was stirred for 3 hours. Cooling from the outside was stopped, and while cooling was carried out by means of the heat of vaporization of liquid ammonia in the reaction liquid, the reaction liquid was stirred. The temperature of the reaction liquid was slowly and naturally increased to room temperature. After it was confirmed that Eu metal had completely reacted, 250 ml of THF was added thereto, and while the oil bath was set to 50° C., the mixture was stirred for 3 hours.

The mixture was left to stand overnight, the supernatant was separated by filtration with a 1-μm fluororesin filter, and the filtrate was distilled off under reduced pressure at 110° C. Thus, 59.2 g of a solid fraction was obtained.

The solid fraction thus obtained was introduced into a simple distillation apparatus, and vacuum distillation was carried out two times at 160° C. to 210° C. and 0.01 torr to 0.1 torr. Thus, a dark red distillate was obtained, and the distillate was solidified at room temperature. The yield amount was 44.3 g (0.0926 mol), and the yield was 68% (based on Eu metal).

The sample thus obtained was subjected to the following analysis.

(1) Composition Analysis

The liquid obtained by wet decomposition was subjected to an ICP atomic emission spectrometric analysis, and as a result, the Eu content was 31.2% (theoretical value: 31.8%).

(2) EI-MS Analysis

An analysis was carried out using a JMS-T100GC type mass analyzer (manufactured by JEOL, Ltd.) under the following measurement conditions: ionization method: EI(+), ion source temperature: 230° C., ionization current: 150 μA, ionization voltage: 70 V, accelerating voltage: 7 kV, and measurement range: m/z 35 to 800.

FIG. 1 illustrates this EI-MS spectrum. As illustrated in FIG. 1, since molecular ions (m/z 479.20) were detected in EI MS, the analyzed sample was identified as $Eu[C_5(CH_3)_4(n-C_3H_7)]_2$.

(3) TG-DTA

TG-DTA measurement was carried out under the following measurement conditions: sample weight: 18.75 mg, atmosphere: Ar at 1 atm, and rate of temperature increase: 10.0° C./rain.

Figure 2:
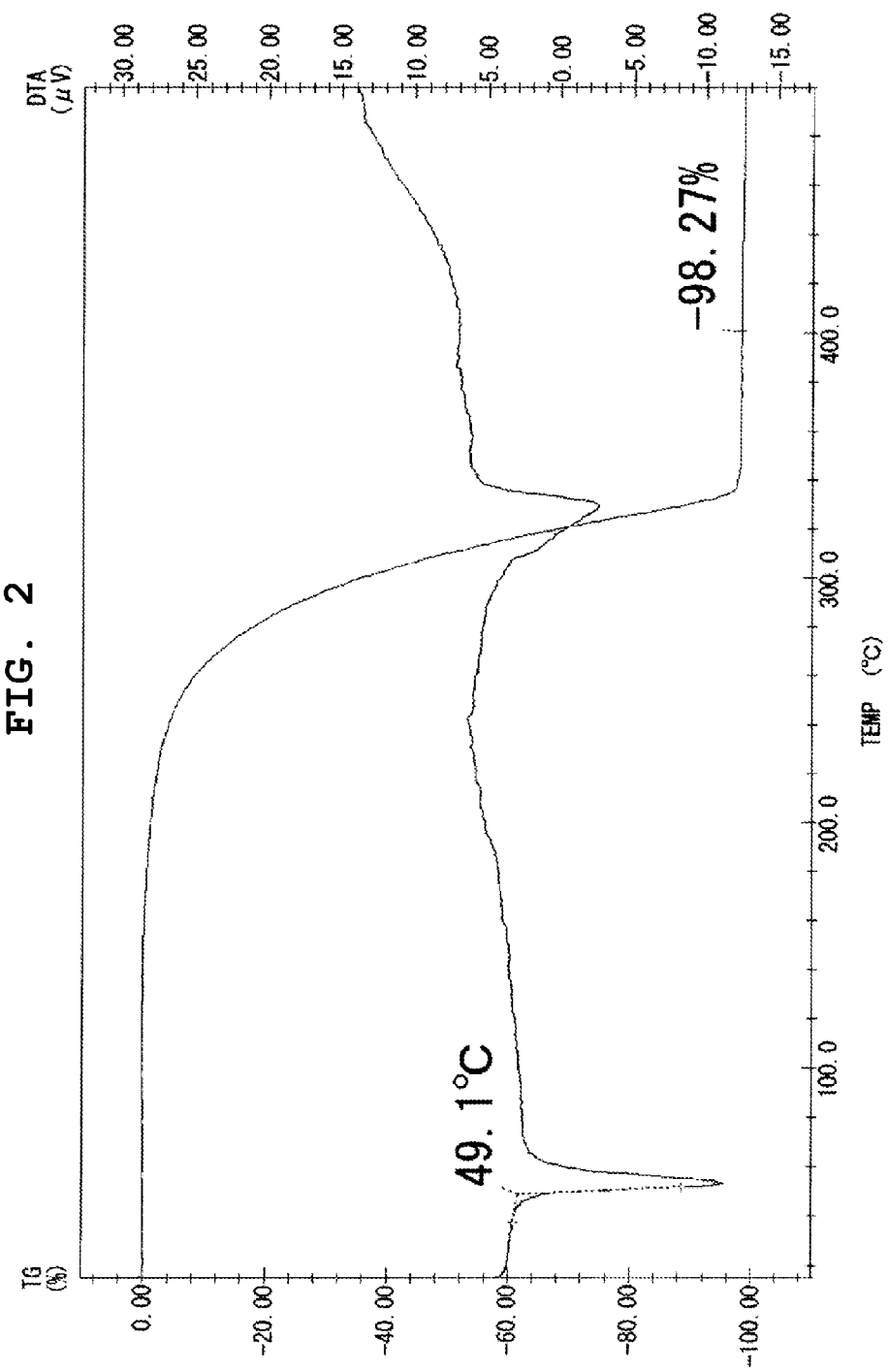
FIG. 2 is a diagram (TG-DTA curve) illustrating the results of a differential thermogravimetric analysis of the sample $(Eu[C_5(CH_3)_4(n-C_3H_7)]_2)$ obtained in Example 1.

FIG. 2 illustrates the results of this TG-DTA measurement. As illustrated in FIG. 2, an endothermic peak that was not associated with a weight change was identified at 49.1° C. This was attributable to the melting of $Eu[C_5(CH_3)_4(n-C_3H_7)]_2$.

Furthermore, it was also confirmed that 98.3% of the compound had evaporated up to 350° C. From this, it can be said that $Eu[C_5(CH_3)_4(n-C_3H_7)]_2$ does not undergo thermal deterioration in a short time in the order of minutes at or below 350° C., and the compound has the thermal stability required from a raw material for an ALD method or a CVD method.

(4) Vapor Pressure

As a result of measurement according to a gas saturation method, the vapor pressure was 0.1 torr/161° C.

Example 2

Synthesis of $Eu[C_5(CH_3)_4(n-C_3H_7)]_2$ (Method of Using Europium Halide as a Raw Material)

In a 2-L flask equipped with Dimroth condenser, 800 ml of THF, 15.5 g (0.646 mol) of NaH, and 101 g (0.615 mol) of $C_5(CH_3)_4(n-C_3H_7)H$ were introduced, and the mixture was allowed to react for 60 hours. Subsequently, any unreacted fraction was separated by filtration. 92.6 g (0.228 mol) of anhydrous $EuI_2$ was added to the filtrate, the oil bath was set at 40° C., and the mixture was heated and stirred for 31 hours.

Next, THF was distilled off, subsequently 1000 ml of toluene and 160 ml of THF were added thereto, and the mixture was heated to reflux. The reaction liquid was cooled to room temperature and filtered, and then the reaction liquid was distilled off under reduced pressure at 110° C. Thus, 62.1 g of a solid fraction was obtained.

The solid fraction thus obtained was introduced into a simple distillation apparatus, and vacuum distillation was carried out two times at 160° C. to 200° C. and 0.01 torr to 0.1 torr. Thus, a dark red distillate fraction was obtained, and the fraction was solidified at room temperature. The yield amount was 22.1 g (0.0462 mol), and the yield was 28% (based on Eu metal).

$Eu[C_5(CH_3)_4(n-C_3H_7)]_2$ obtained by distillation was subjected to a composition analysis in the same manner as in Example 1. The content of Eu metal was 31.3% (theoretical value: 31.8%).

Example 3

Formation of $Eu_2O_3$ Film According to an ALD Method Using $Eu[C_5(CH_3)_4(n-C_3H_7)]_2$ A cylinder filled with 30 g of $Eu[C_5(CH_3)_4(n-C_3H_7)]_2$ obtained in Example 1 was subjected to bubbling with 100 sccm of Ar gas (pulse A), while the cylinder was heated to 170° C. On the other hand, a cylinder filled with water was subjected to bubbling with 50 sccm of Ar gas (pulse B), while the cylinder was heated to 20° C. 200 sccm of Ar was allowed to flow as a purging gas, and an ALD operation was carried out under the conditions of 1 second of pulse introduction and 3 seconds of purging.

In an ALD chamber at a pressure of about 5 torr, a Si substrate at a substrate temperature of 300° C. was placed, and 100 cycles of a process of (introduction of pulse A→purging→introduction of pulse B→purging) were carried out. Thus, a $Eu_2O_3$ film having a thickness of 10 nm was obtained.

Meanwhile, even in the case where film formation was carried out in the same manner as above by setting the amount of filling of $Eu[C_5(CH_3)_4(n-C_3H_7)]_2$ to 5 g, there was no difference in the rate of film formation with the case of setting the amount of filling to 30 g, and it was confirmed that there is no variation in the amount of supply depending on the status of use.

Example 4

Synthesis of $Eu[C_5(CH_3)_4(C_2H_5)]_2$

Synthesis was carried out in the same manner as in Example 1, except that $C_5(CH_3)_4(C_2H_5)H$ was used instead of $C_5(CH_3)_4(n-C_3H_7)H$, and $Eu[C_5(CH_3)_4(C_2H_5)]_2$ was obtained at a yield of 53.5%. The compound was a solid which was immediately decomposed when brought into contact with moisture or oxygen in the atmosphere.

The vapor pressure observed during the distillation operation was 0.02 torr/152° C.

Figure 3:
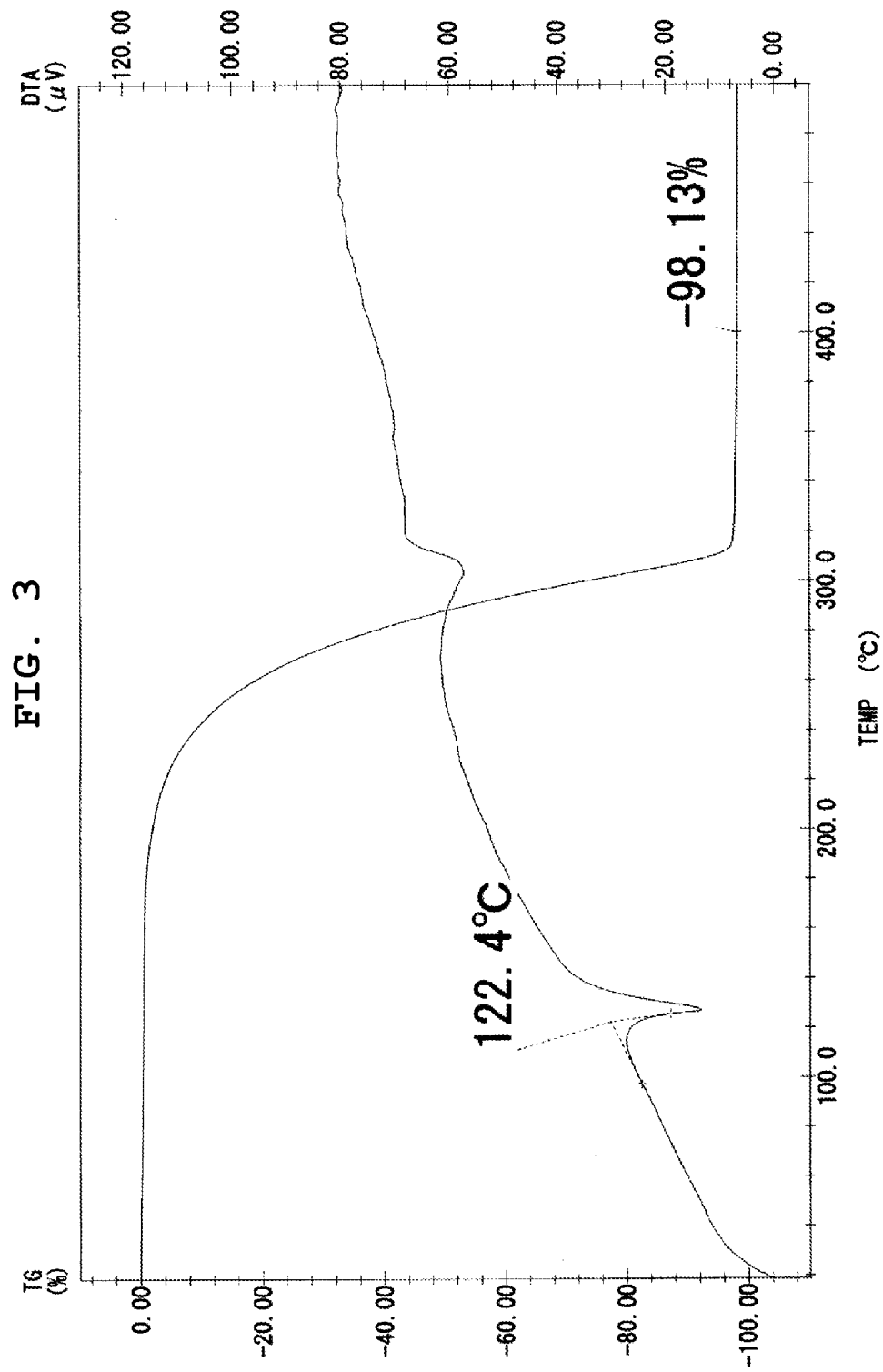
FIG. 3 is a diagram (TG-DTA curve) illustrating the results of a differential thermogravimetric analysis of a sample (Eu$[C_5(CH_3)_4(C_2H_5)]_2$) obtained in Example 3.

FIG. 3 illustrates the results of TG-DTA measurement. As illustrated in FIG. 3, a melting point was observed at 122.4° C. Also, it was confirmed that the compound did not undergo thermal decomposition up to 350° C., and 98.13% thereof had evaporated.

From the results of an analysis on the reactivity with an oxidizing agent such as water or oxygen, vapor pressure, melting point, and thermal stability, it was recognized that this compound had properties that are suitable as a precursor for forming a europium-containing thin film according to a CVD method or an ALD method.

Example 5

Synthesis of $Eu[C_5(CH_3)_4(n-C_4H_9)]_2$

Synthesis was carried out in the same manner as in Example 1, except that $C_5(CH_3)_4(n-C_4H_9)H$ was used instead of $C_5(CH_3)_4(n-C_3H_7)H$, and $Eu[C_5(CH_3)_4(n-C_4H_9)]_2$ was obtained at a yield of 35.4%. The compound was a solid which was immediately decomposed when brought into contact with moisture or oxygen in the atmosphere.

The vapor pressure observed during the distillation operation was 0.25 torr/172° C.

Figure 4:
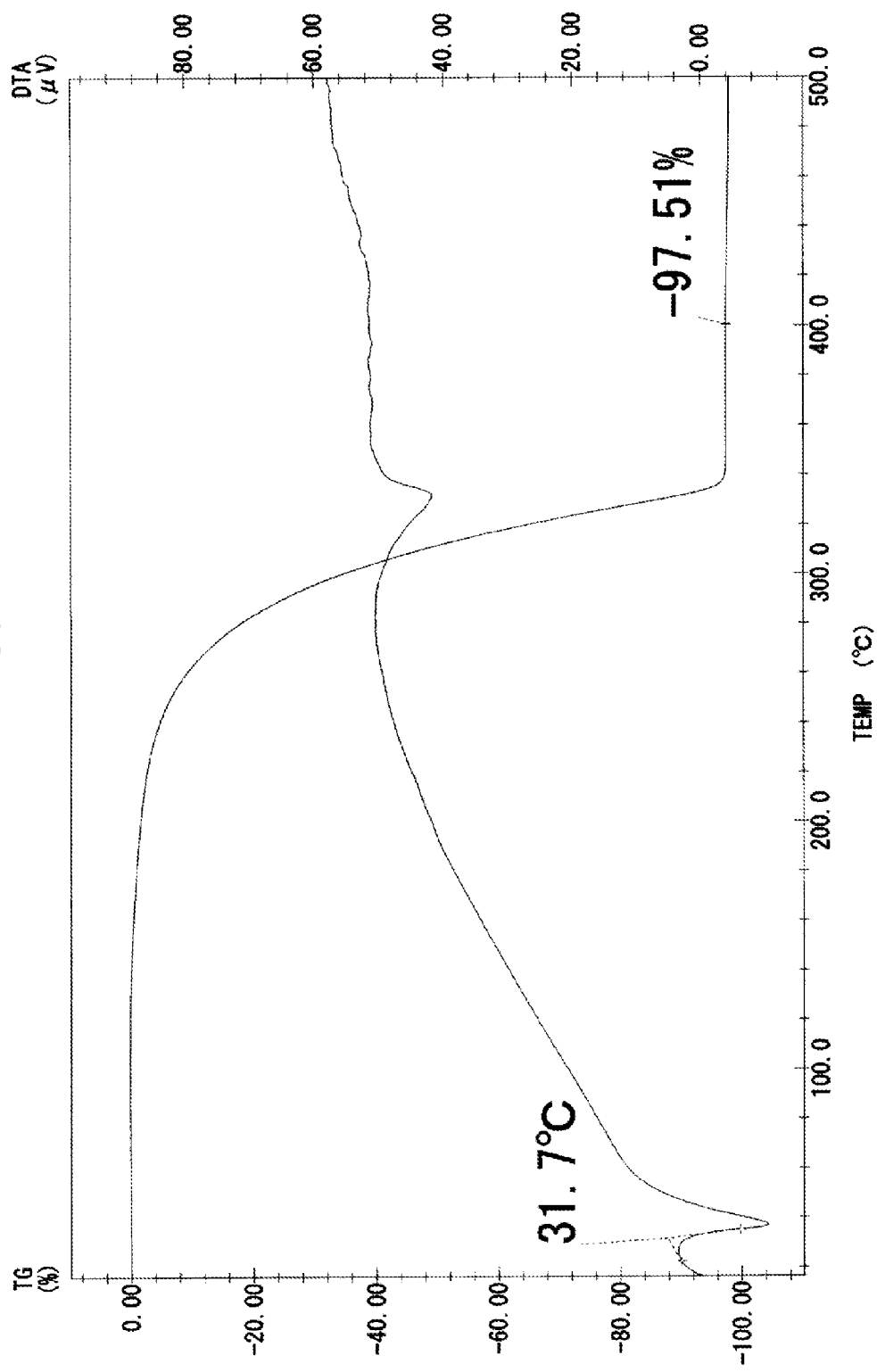
FIG. 4 is a diagram (TG-DTA curve) illustrating the results of a differential thermogravimetric analysis of a sample (Eu$[C_5(CH_3)_4(n-C_4H_9)]_2$) obtained in Example 4.

FIG. 4 illustrates the results of TG-DTA measurement. As illustrated in FIG. 4, a melting point was observed at 31.7° C. Also, it was confirmed that the compound did not undergo thermal decomposition up to 350° C., and 97.51% thereof had evaporated.

From the results of an analysis on the reactivity with an oxidizing agent such as water or oxygen, vapor pressure, melting point, and thermal stability, it was recognized that this compound had properties that are suitable as a precursor for forming a europium-containing thin film according to a CVD method or an ALD method.

Example 6

Synthesis of $Eu[C_5(CH_3)_4(n-C_5H_{11})]_2$

Synthesis was carried out in the same manner as in Example 1, except that $C_5(CH_3)_4(n-C_5H_{11})H$ was used instead of $C_5(CH_3)_4(n-C_3H_7)H$, and $Eu[C_5(CH_3)_4(n-C_5H_{11})]_2$ was obtained at a yield of 38.6%. The compound was a liquid that was highly viscous at room temperature, and was immediately decomposed when brought into contact with moisture or oxygen in the atmosphere.

The vapor pressure observed during the distillation operation was 0.01 torr/155° C.

Figure 5:
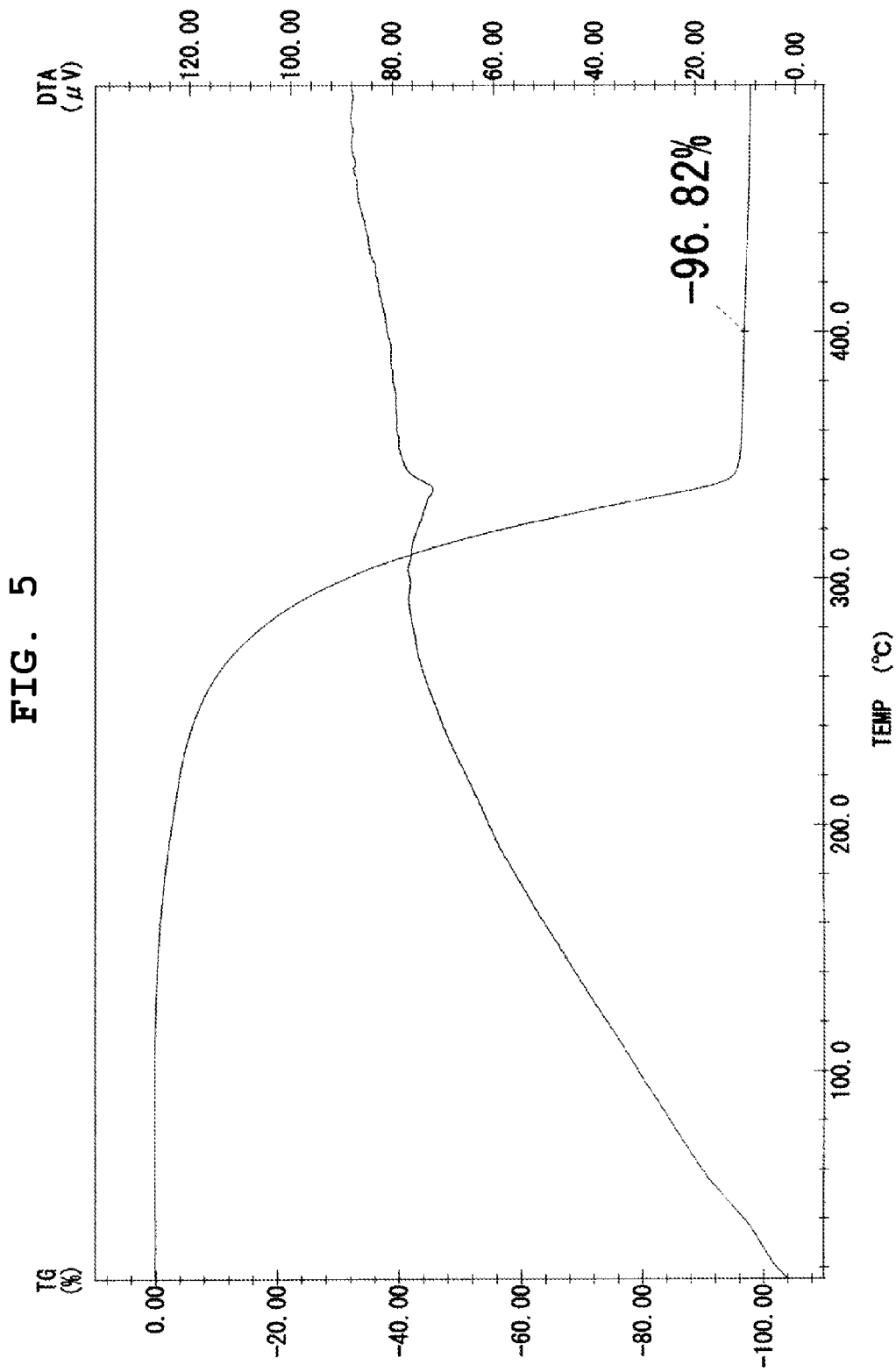
FIG. 5 is a diagram (TG-DTA curve) illustrating the results of a differential thermogravimetric analysis of a sample (Eu$[C_5(CH_3)_4(n-C_5H_{11})]_2$) obtained in Example 5.

FIG. 5 illustrates the results of TG-DTA measurement. As illustrated in FIG. 5, it was confirmed that the compound did not undergo thermal decomposition up to 400° C., and 96.82% thereof had evaporated.

From the results of an analysis on the reactivity with an oxidizing agent such as water or oxygen, vapor pressure, melting point, and thermal stability, it was recognized that this compound had properties that are suitable as a precursor for forming a europium-containing thin film according to a CVD method or an ALD method.

Comparative Example 1

Synthesis of $Eu[C_5(CH_3)_5]_2$

In a 300-ml four-necked flask, 100 ml of dehydrated toluene, 6.4 g (0.042 mol) of Eu metal, and 22.8 g (0.167 mol) of $C_5(CH_3)_5H$ were introduced, and the mixture was cooled to a temperature of −70° C. or lower. While about 50 g of ammonia gas was slowly blown into this mixture, the mixture was stirred for 3 hours. Cooling from the outside was stopped, and while cooling was carried out by means of the heat of vaporization of liquid ammonia in the reaction liquid, the reaction liquid was stirred. The temperature of the reaction liquid was slowly and naturally increased to room temperature. After it was confirmed that Eu metal had completely reacted, 100 ml of THF was added thereto, and while the oil bath was set to 50° C., the mixture was stirred for 3 hours.

The mixture was left to stand overnight, the supernatant was separated by filtration with a 1-μm fluororesin filter, and the filtrate was distilled off under reduced pressure at 110° C. Thus, a brown solid fraction was obtained.

The solid fraction thus obtained was placed in a sublimation apparatus, and purification by sublimation was carried out two times at 240° C. and 0.01 torr to 0.1 torr. Thus, a dark violet solid was obtained. The yield amount was 8.5 g, and the yield was 48%.

Figure 6:
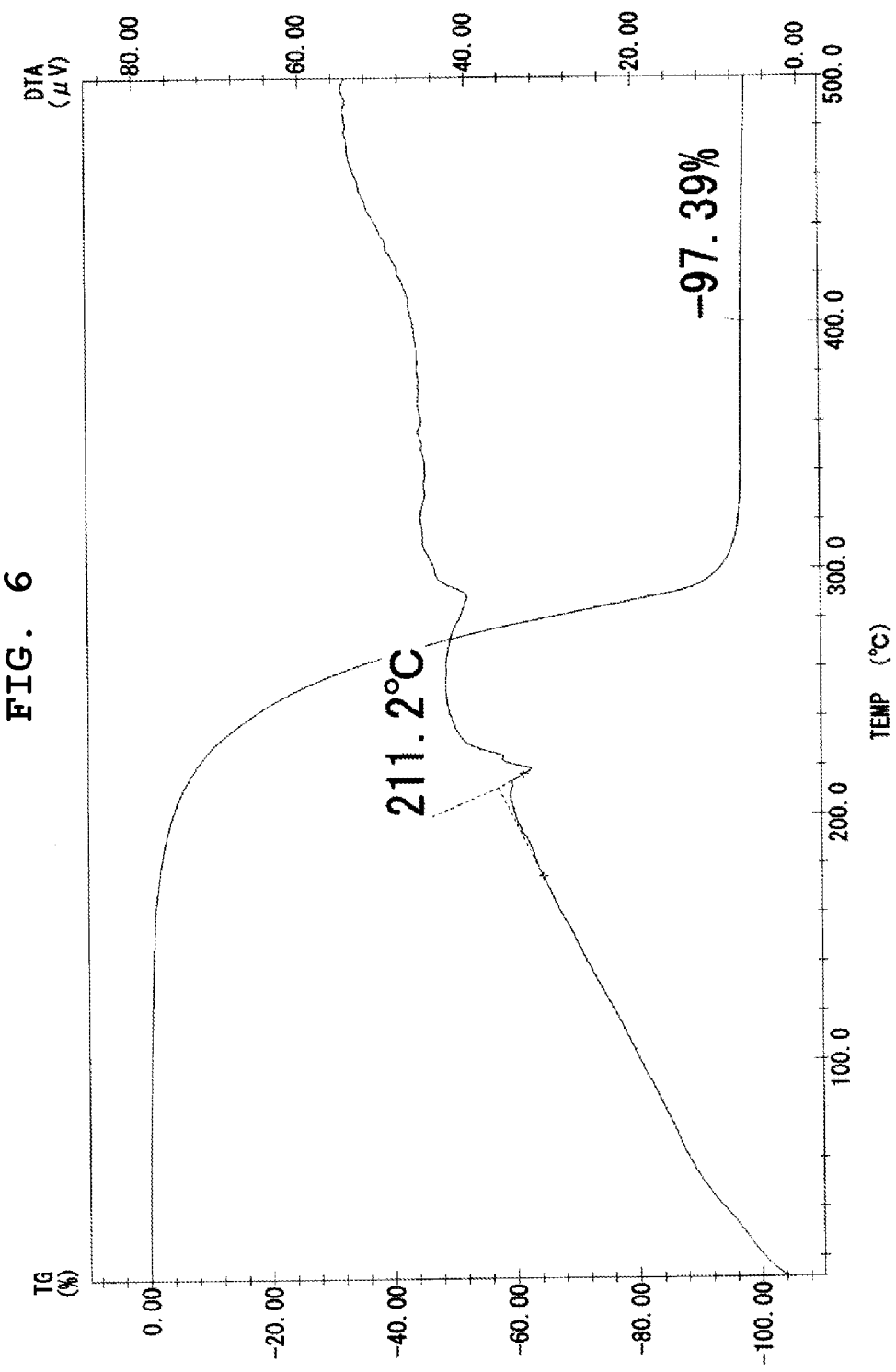
FIG. 6 is a diagram (TG-DTA curve) illustrating the results of a differential thermogravimetric analysis of a sample (Eu$[C_5(CH_3)_5]_2$) obtained in Comparative Example 1.

FIG. 6 illustrates the results of TG-DTA measurement. As illustrated in FIG. 6, a melting point was observed at 211.2° C. As can be seen from these results, it is difficult for this compound to be supplied by bubbling, and purification by distillation is also difficult.

The invention claimed is:

1. Bis(tetramethylmonoalkylcyclopentadienyl)europium represented by formula:

$Eu[C_5(CH_3)_4R]_2$ (wherein R represents an alkyl group having 2 or more carbon atoms).

2. Bis(tetramethylmonoalkylcyclopentadienyl)europium according to claim 1, wherein R is an alkyl group having 2 to 5 carbon atoms.

3. Bis(tetramethylmonoalkylcyclopentadienyl)europium according to claim 1, wherein R represents any of an ethyl group, an n-propyl group, an n-butyl group and an n-pentyl group.

4. A precursor for forming a europium-containing thin film according to a chemical vapor deposition method or an atomic layer deposition method, the precursor being bis(tetramethylmonoalkylcyclopentadienyl)europium according to claim 1.

5. A method for forming a europium-containing thin film, using the precursor for forming a europium-containing thin film according to claim 4.

6. Bis(tetramethylmonoalkylcyclopentadienyl)europium according to claim 2, wherein R represents any of an ethyl group, an n-propyl group, an n-butyl group and an n-pentyl group.

7. A precursor for forming a europium-containing thin film according to a chemical vapor deposition method or an atomic layer deposition method, the precursor being bis(tetramethylmonoalkylcyclopentadienyl)europium according to claim 2.

8. A precursor for forming a europium-containing thin film according to a chemical vapor deposition method or an atomic layer deposition method, the precursor being bis(tetramethylmonoalkylcyclopentadienyl)europium according to claim 3.

* * * * *